United States Patent [19]

Mizushima et al.

[11] Patent Number: 5,171,566
[45] Date of Patent: Dec. 15, 1992

[54] FLURBIPROFEN DERIVATIVE OPHTHALMIC PREPARATION

[75] Inventors: Yutaka Mizushima, Tokyo; Hiroyuki Okamoto, Kobe; Shigetoshi Sugio, Hirakata; Kazumasa Yokoyama, Toyonaka; Tadakazu Suyama, Tsuzuki; Masao Tohno, Otsu; Makoto Okumura, Moriyama; Yoshiaki Konishi, Soraku; Kiyonoshin Ichikawa, Omihachiman; Katsuhiro Uchida, Kyoto, all of Japan

[73] Assignee: The Green Cross Corporation, Osaka, Japan

[21] Appl. No.: 667,354

[22] Filed: Mar. 6, 1991

Related U.S. Application Data

[63] Continuation of Ser. No. 49,353, May 14, 1987, abandoned.

[30] Foreign Application Priority Data

May 16, 1986 [JP] Japan ................................. 61-113383

[51] Int. Cl.$^5$ .................... A61K 31/235; A61K 31/74
[52] U.S. Cl. ................... 424/78.04; 514/570
[58] Field of Search ...................... 514/570; 424/78.04

[56] References Cited

U.S. PATENT DOCUMENTS

| | | | |
|---|---|---|---|
| 4,230,724 | 10/1980 | Cooper et al. | 514/570 |
| 4,309,421 | 1/1982 | Ghyczg et al. | 514/570 |
| 4,559,343 | 12/1985 | Han et al. | 514/264 |
| 4,613,505 | 9/1986 | Mizushima et al. | 424/80 |
| 4,687,762 | 8/1987 | Zukeshima et al. | 514/34 |

FOREIGN PATENT DOCUMENTS 0129435 12/1984 European Pat. Off. .
59-13720 1/1984 Japan .

OTHER PUBLICATIONS

Trans. of Kokai 59-13720.

Primary Examiner—Thurman K. Page
Assistant Examiner—Peter F. Kulkosky
Attorney, Agent, or Firm—Cushman, Darby & Cushman

[57] ABSTRACT

There is provided an ophthalmic preparation comprising a fat emulsion containing flurbiprofen or its derivative such as ester as an active ingredient.

3 Claims, No Drawings

FLURBIPROFEN DERIVATIVE OPHTHALMIC PREPARATION

This is a continuation of application Ser. No. 07/49,353, filed on May 14, 1987 now abandoned.

This invention relates to an ophthalmic preparation comprising a fat emulsion containing flurbiprofen (hereinafter sometimes referred to as "FP") or its derivative.

Flurbiprofen [chemical name: 2-(2-fluoro-4-biphenylyl)propionic acid] has superior antiinflammatory, analgetic and antipyretic activities and has been sold in the form of tablets.

FP is sparingly soluble in water and hence, some means in formulation are required for administration as ophthalmic lotion to inflammation of eyes.

For formulation of FP as ophthalmic lotion, there have been known a method of formation of its salt (Japanese Patent Unexamined Publication No. 102817/82) and a method of forming a clathrate with cyclodextrin (Japanese Patent Unexamined Publication No. 126810/83).

For ophthalmic preparation containing FP or its derivative, it is important that FP or its derivative can sufficiently migrate to the anterior chamber of the eye.

Furthermore, solubility, stability and stimulation are important for ophthalmic preparation, especially ophthalmic lotion.

Accordingly, the object of this invention is to provide an ophthalmic preparation containing FP or its derivative which effectively migrates to the anterior chamber and besides is excellent in solubility in aqueous solvents, storage stability and non-stimulation of the eye.

The inventors have made intensive researches in an attempt to solve the above problems and found that the above object can be attained by using a fat emulsion of FP or its derivative as an ophthalmic preparation.

That is, this invention relates to an ophthalmic preparation comprising a fat emulsion containing FP or its derivative as an active ingredient.

The FP derivatives used in this invention have no special limitation as long as they have an activity as FP and can be soluble in soybean oil and emulsified into a fat emulsion and some of the derivatives as well as the fat emulsion thereof are known, for example, in Japanese Patent Unexamined Publication Nos. 13720/84 and U.S. Pat. No. 4,613,505, in either of which no mentions are made of ophthalmic preparations of the fat emulsion.

One of the derivatives is an ester of FP and is disclosed in U.S. Pat. No. 4,613,505.

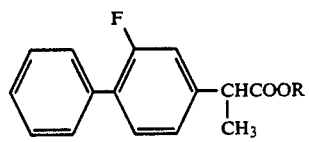

(1)

wherein R is an alkylcarbonyloxyalkyl group or an alkenylcarbonyloxyalkyl group represented by the formula (A)

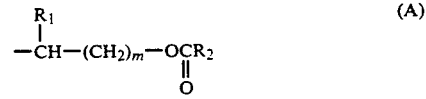

wherein $R_1$ is a hydrogen atom or a $C_1$–$C_3$ alkyl group. $R_2$ is a $C_1$–$C_{15}$ alkyl group or a $C_2$–$C_8$ alkenyl group, and m is zero or an integer of 1; or a lactone group represented by the formula (B)

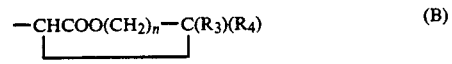

wherein $R_3$ and $R_4$ are the same as or different from each other and are a hydrogen atom or a $C_1$–$C_3$ alkyl group, and n is an integer of 1 or 2.

Typical examples of the group represented by R in the general formula (I), which falls in the formula (A), include acetoxymethyl group, propionyloxymethyl group, isobutyryloxymethyl group, pivaloyloxymethyl group, palmitoyloxymethyl group, crotonoyloxymethyl group, 3,3-dimethylacryloyloxymethyl group, 1-acetoxyethyl group, 1-acetoxypropyl group, 1-propionyloxyethyl group, 1-isobutyryloxyethyl group, 1-pivaloyloxyethyl group, 1-palmitoyloxyethyl group, 1-crotonoyloxyethyl group, 1-(3,3-dimethylacryloyloxy)ethyl group, 1-(2,4-hexadienoyloxy)ethyl group, 2-acetoxyethyl group, 2-propionyloxyethyl group, 2-crotonoyloxyethyl group, 2-(3,3-dimethylacryloyloxy)ethyl group, 2-(2,4-hexadienoyloxy)ethyl group and 2-(3,7-dimethyl-2,6-octadienoyloxy)ethyl group, and the lactone groups which falls in the formula (B) are 3,3-dimethyl-γ-butyrolacton-2-yl group, 3,3-dimethyl-γ-valerolacton-2-yl group and 3-methyl-3-propyl-γ-butyrolacton-2-yl group.

Of the esters defined in the above formula, a lower alkanoyloxy-lower alkyl ester such as 1-acetoxyethyl (or methyl) 2-(2-fluoro-4-biphenyl)propionate is preferable.

Another of the derivatives suitably used in the invention is an alkyl ester of FP as is disclosed in Japanese Patent Unexamined Publication No. 13720/84. The alkyl of the ester is selected from $C_1$–$C_{18}$ alkyls which may be straight or branched form.

Composition of the fat emulsion suitably in this invention comprises generally 0.001–5% (W/V), preferably 0.01–1% (W/V) of FP or its derivative, 0.1–50% (W/V), preferably 1–20% (W/V) of soybean oil, 1–50 parts, preferably 5–30 parts of phospholipid based on 100 parts by weight of the soybean oil and a suitable amount of an aqueous solvent, the FP or its derivative being dissolved in soybean oil emulsified.

As soybean oil, there may be generally used a purified soybean oil of high purity, which is disclosed, for example, in Journ. Am. Oil Chemist Soc. 27 422–423. Furthermore, as the phospholipid, there may also be generally used a purified phospholipid or a hydrogenated phospholipid which are derived from soybean or egg yolk, as disclosed in Journ. Biol. Chem. 192 723–628 (1951).

There may be used any aqueous solvents which are physiologically acceptable such as, for example, distilled water for injection, physiological saline solution, phosphate buffer solution, borate buffer solution, citrate buffer solution, etc.

The fat emulsion of this invention may further contain up to 0.3% (W/V) of a fatty acid having 6-22, preferably 12-20 carbon atoms or a physiologically acceptable salt thereof as an emulsion adjuvant. These fatty acids and salts thereof may be known ones. The emulsion may also contain 0.5% (W/V) or less, preferably 0.1% or less of a cholesterol or 5% (W/V) or less, preferably 1% (W/V) or less of phosphatidic acid as a stabilizer.

Furthermore, the preparation of this invention may also contain as a stabilizer a high molecular substance selected from albumin, dextran, vinyl polymer such as a polyvinyl pyrrolidone, nonionic surface active agent such as a polyalkylene glycol of a molecular weight of 1,000 to 10,000 and a polyoxyethylene-polyoxypropylene copolymer of a molecular weight of 1,000 to 20,000, gelatin and hydroxyethyl starch. Amount of the stabilizer added is 0.1-5 parts by weight, preferably 0.5-1 part by weight based on one part by weight of FP or its derivative. The preparation of the fat emulsion is concretely disclosed, for example, in U.S. Pat. No. 4,613,505.

The fat emulsion of this invention may be prepared by using an ordinary homogenizer, for example, a pressure-jet type homogenizer or an ultrasonic homogenizer. That is, predetermined amounts of soybean oil, a phospholipid, FP or its derivative and, if necessary, other additives as mentioned above are mixed and the mixture is heated to form a solution, which is subjected to homogenizing treatment to form a water-in-oil type dispersion. A required amount of water is added to this dispersion and this is again subjected to homogenizing treatment by the homogenizer to convert the dispersion into an oil-in-water type emulsion. Stabilizer may be added to the thus obtained emulsion.

Average particle size of the fat emulsion in this invention is preferably 1.0 $\mu$ or less (particle size distribution 0.1-1.0 $\mu$).

Specific embodiments of the preparation of this invention are, for example, ophthalmic lotions, ointments, etc.

As ophthalmic lotions, the fat emulsion obtained as above may be used as it is in the form of a liquid preparation or may be formulated by freeze-drying by conventional method. The freeze-dried preparation is generally diluted with or dispersed in a physiological aqueous solution for use.

The ophthalmic lotion is preferably isotonic. For isotonification, it is also possible to add a conventional isotonifying agent such as glycerine, glucose, salts (e.g., boric acid, sodium chloride, etc.). The isotonifying agent may be added during the preparation of the fat emulsion.

It is also possible as a matter of course to use additives added in the preparation of ordinary ophthalmic lotions (preservatives such as methyl paraoxybenzoic acid, propyl paraoxybenzoic acid, sodium dehydroacetate, thimerosal, etc.; thickening agents such as polyvinyl pyrrolidone, sodium polyacrylate, etc.).

The pH of the ophthalmic lotion is usually about 5-9, preferably about 6-8.

The ophthalmic lotion may be preserved at room temperature even in a diluted form as if an aqueous solution, but preferably is preserved at a lower temperature of about 4° C. The ophthalmic lotion is administered in the dosage form of dropping lotion or eye perfusion.

Ophthalmic ointment is prepared, for example, by mixing and dispersing freeze-dried powders of the fat emulsion in an ointment base.

The ointment base may be any of known ones and may be either of aqueous base or oily base. Typical examples thereof are vaseline, polyethylene glycol, etc.

The preparation of this invention may be sterilized by any known methods, for example, heat-steam sterilization, filtration sterilization, etc.

The dose of the emulsion preparation of this invention varies depending on sex, age, symptoms of patients, but generally is administered at a dose of 0.04- 1-2.0 ml/day in terms of fat emulsion and 0.1-1000 $\mu$g/day in terms of FP in about 1-10 times.

When the emulsion preparation of this invention is applied, FP or its derivative contained therein effectively migrates into anterior chamber and thus the preparation is effective for treatment of inflammation of the conjunctiva, coroneal epithelium.

Furthermore, the preparation has little toxicity and gives substantially no stimulus to the eye and besides is excellent in stability in aqueous solvent and storage stability. Therefore, this is markedly superior as ophthalmic preparation, especially ophthalmic lotion.

The following nonlimiting examples and test examples further illustrate this invention.

EXAMPLE 1

To 200.0 g of purified soybean oil were added 24.0 g of purified egg yolk phospholipid, 2 g of flurbiprofen, 0.5 g of sodium oleate and 0.5 g of phosphatidic acid and the mixture was heated at 40°-75° C. to form a solution. To this solution was added 1000 ml of distilled water. This mixture was emulsified by passing it through a Manton-Gaulin type homogenizer under pressure of 100 kg/cm$^2$ in the first stage and 10 times under total pressure of 450 kg/cm$^2$. Then, to this emulsion was added 44.2 g of glycerine and 730 ml of distilled water for injection of 20°-40° C. and then, the mixture was treated with a homomixer to obtain a crude emulsion. This crude emulsion was again emulsified by passing it through a Manton-Gaulin type homogenizer under pressure of 120 kg/cm$^2$ in the first stage and 10 times under total pressure of 500 kg/cm$^2$. Thus, a homogenized extremely fine fat emulsion containing flurbiprofen (pH 7) was obtained.

EXAMPLE 2

To 20 g of purified soybean oil was added 0.4 g of flurbiprofen cetyl ester to form a solution at 80° C. Then, to the solution was added 5 g of purified egg yolk phospholipid and this mixture was vigorously stirred at 80° C. to form a solution, followed by adding 200 ml of distilled water and stirring by homomixer to form a crude emulsion. This crude emulsion was emulsified as in Example 1 under high pressure by a Manton-Gaulin type homogenizer to obtain an extremely fine fat emulsion (pH 7) containing flurbiprofen cetyl ester.

EXAMPLE 3

To 30 g of purified soybean oil were added 3.6 g of a phospholipid, 3 mg of acetoxymethyl 2-(2-fluoro-4-biphenylyl)propionate, 0.15 g of sodium oleate and 0.15 g phosphatidic acid and the mixture was heated at 40°-75° C. to form a solution. The solution was mixed with 200 ml of distilled water and then 7.5 g of glycerol (Japanese Pharmacopoeia), made up into a total volume of 300 ml with distilled water for injection of 20°-40° C.

and then treated with a homomixer to form a crude emulsion.

The crude emulsion was then emulsified by passing it through a Manton-Gaulin type homogenizer under pressure of 120 kg/cm² in the first stage and 10 times under total pressure of 500 kg/cm². Thus, a homogenized, extremely fine fat emulsion (pH 7) was obtained. The emulsion had an average particle diameter of 0.2-0.4 μm and contained no particles larger than 1 μm.

EXAMPLE 4

Example 3 was repeated except that 1-acetoxyethyl 2-(2-fluoro-4-biphenylyl)propionate was used in place of acetoxymethyl 2-(2-fluoro-4-biphenylyl)propionate. As a result, a homogenized, extremely fine fat emulsion (pH 7) was obtained. The emulsion had an average particle diameter of 0.2-0.4 μm and contained no particles larger than 1 μm.

EXAMPLE 5

In the same manner as in Example 1 a fat emulsion was obtained from the following compositions. This emulsion had a pH of 7.5.

| | |
|---|---|
| 1-Acetoxyethyl 2-(2-fluoro-4-biphenylyl)propionate | 0.1% (W/V) |
| Soybean oil | 10% (W/V) |
| Egg yolk phospholipid | 1.2% (W/V) |
| Glycerol | 2.21% (W/V) |
| Disodium hydrogen phosphate | 0.0284% (W/V) |
| Citric acid | 0.0961% (W/V) |
| Purified water | balance amount |

TEST EXAMPLE 1

TOXICITY IN APPLICATION OF OPHTHALMIC LOTION

The fat emulsion of the FP derivative obtained in Example 4 was tested on toxicity in application of the emulsion as an ophthalmic lotion using white rabbits in accordance with the Draise method (Jour. Pharmacol. Exp. Ther. 83 377-390 (1944). Physiological saline solution was used as a control and each of the FP-sodium salt and FP-cyclodextrin solutions were used as control chemicals. As a result, it has been found that the toxicity of the fat emulsion is similar to that of the physiological saline solution and is much lower than those of the control chemicals.

TEST EXAMPLE 2

50 μl of each of the following ophthalmic lotions as shown below [containing 0.1% (W/V) in terms of FP] was dropped in the eyes of white rabbits and after one hour, aqueous humor was collected and concentration of FP in the aqueous humor was measured by HPLC. The results are shown in Table 1. The results indicates that the FP sufficiently migrates into the anterior chamber and anti-inflammation and analgetic effects can be expected.

TABLE 1

| Ophthalmic lotion | Concentration of PF (μg/ml) |
|---|---|
| FP fat emulsion (Example 1) | 1.0 |
| Derivative emulsion (Example 4) | 1.3 |

What is claimed is:

1. A method of ophthalmic treatment which comprises applying to an inflamed eye an ophthalmic composition including a fat emulsion containing a phospholipid emulsifier and emulsified soybean oil in which a flurbiprofen derivative is dissolved, the derivative being a soybean oil-soluble ester of flurbiprofen represented by the formula:

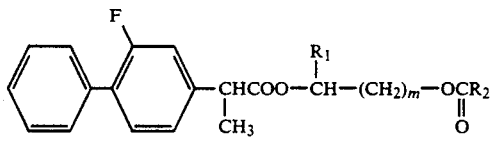

wherein $R_1$ is a hydrogen atom or a $C_1$-$C_3$ alkyl group, $R_2$ is a $C_1$-$C_{15}$ alkyl group or a $C_2$-$C_8$ alkenyl group, and m is zero or an integer of 1;

the fat emulation containing 0.001-5% (W/V) of flurbiprofen derivative, 1-20% (W/V) of soybean oil, 1-50 parts by weight of phospholipid based on 100 parts by weight phospholipid based on 100 parts by weight soybean oil and the balance aqueous medium and a ophthalmologically acceptable carrier.

2. A method according to claim 1 wherein the composition is in the form of a lotion or an ointment.

3. A method according to claim 1 wherein the dosage of the ophthalmic preparation is 0.1-1000 ug/day in terms of flurbiprofen.

* * * * *